United States Patent [19]

Morgan

[11] Patent Number: 5,380,328
[45] Date of Patent: Jan. 10, 1995

[54] COMPOSITE PERFORATED IMPLANT STRUCTURES

[75] Inventor: Frank H. Morgan, Las Vegas, Nev.

[73] Assignee: TiMesh, Inc., Las Vegas, Nev.

[21] Appl. No.: 103,541

[22] Filed: Aug. 9, 1993

[51] Int. Cl.⁶ .............................................. A61F 2/28
[52] U.S. Cl. ..................................... 606/70; 623/16
[58] Field of Search ........................ 128/897–899; 606/69–71, 86, 104; 623/11, 16–23, 66

[56] References Cited

U.S. PATENT DOCUMENTS

| | | | |
|---|---|---|---|
| 3,710,789 | 1/1973 | Ersek | 606/69 X |
| 4,978,355 | 12/1990 | Frey et al. | 623/16 |
| 5,030,233 | 7/1991 | Ducheyne | 623/16 |
| 5,032,445 | 7/1991 | Scantlebury et al. | 604/890.1 X |
| 5,034,186 | 7/1991 | Shimamune et al. | 623/16 X |
| 5,084,051 | 1/1992 | Tormala et al. | 623/16 X |
| 5,108,432 | 4/1992 | Gustavson | 623/16 |
| 5,198,308 | 3/1993 | Shetty et al. | 623/16 X |
| 5,222,987 | 6/1993 | Jones | 623/16 X |

Primary Examiner—Angela D. Sykes
Attorney, Agent, or Firm—Philip D. Junkins

[57] ABSTRACT

A composite surgical implant structure for use orthognathic and reconstructive surgery, for the correction cranial defects, and for reconstructive preprosthetic oral maxillofacial surgery, the implant structure is comprised of at least one layer of perforated, biocompatible metallic sheet material (preferably pure pliable titanium) and at least one layer of biologically and chemically inert microporous membrane material in intimate contact with, and supported by, the layer of perforated metallic sheet material. The microporous membrane material is comprised of randomly dispersed polytetrafluoroethylene fibers, or mixtures of cellulose acetate and cellulose nitrate fibers, or polyvinylidine difluoride fibers and the material has a pore size such that desired biological nutrients are permitted passage through the implant structure and unwanted biological cells are precluded from passage therethrough, The layers of perforated metallic sheet material and microporous membrane material are maintained together to form the composite structure by a biocompatible adhesive, heat fusion of the fibers of the membrane material or mechanical fasteners interacting between the layers. The implant structure is particularly applicable to use for the guided regeneration and enlargement of bone tissue at surgical sites.

16 Claims, 2 Drawing Sheets

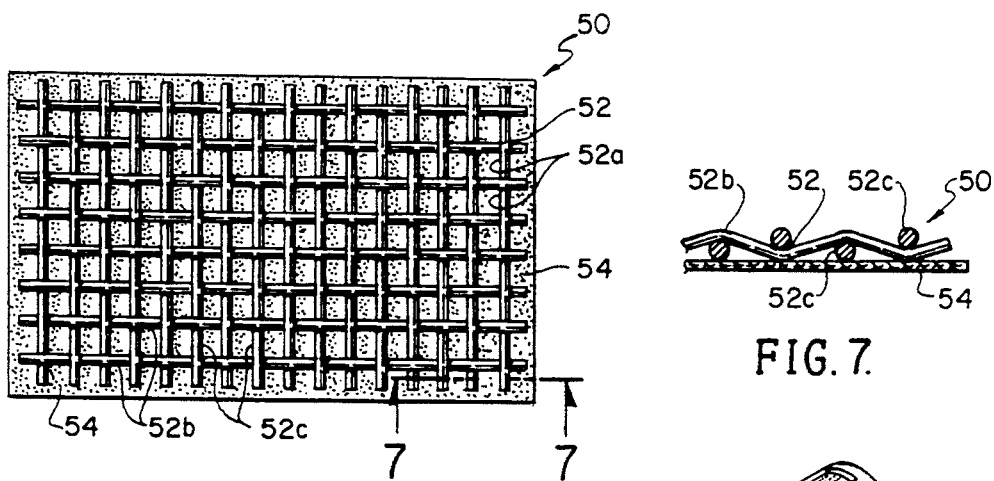
FIG. 6.
FIG. 7.
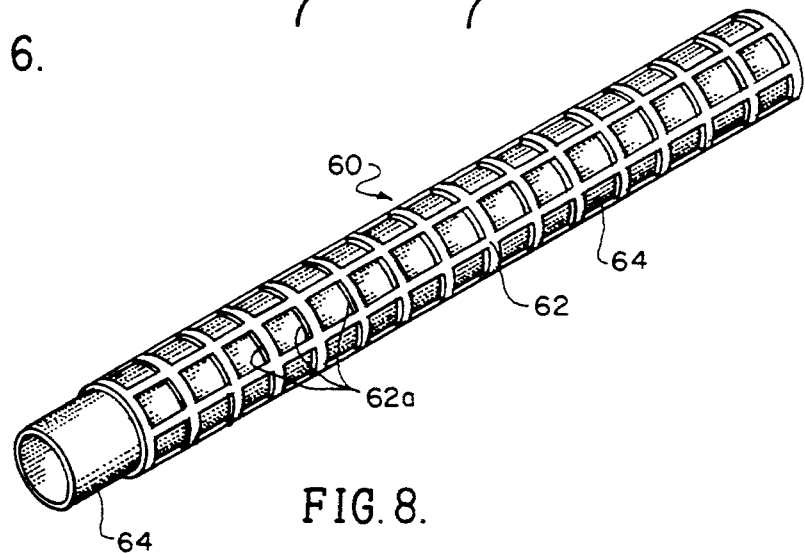
FIG. 8.
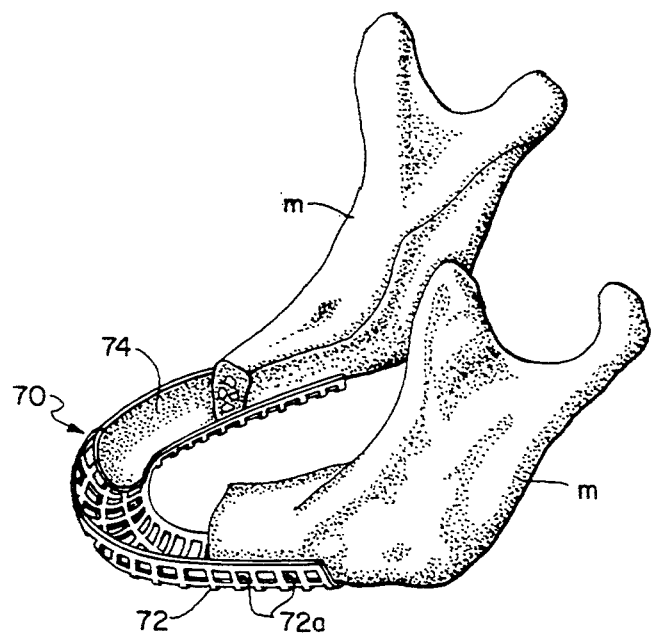
FIG. 9.

COMPOSITE PERFORATED IMPLANT STRUCTURES

FIELD OF THE INVENTION

The present Invention relates to perforated metallic implant structures for use in orthognathic and reconstructive surgery. More particularly, the invention relates to metallic mesh and grid implant structures for use in orthognathic and reconstructive surgery and the correction of cranial defects and for use in the guided regeneration and enlargement of bone tissue.

BACKGROUND OF THE INVENTION

Over the past ten years there has been an increasing interest in, and use of, perforated biocompatible metallic strips and panels as a means for rigid internal fixation of fractures in trauma surgery, as a plate material for bone part immobilization and stabilization, and as bone graft support material in orthognathic and reconstructive surgery. Of particular interest has been the use of perforated strips and panels of titanium as an unequaled implant material in use clinically for over 30 years with no documented cases of allergic reactions or rejections by interfacing tissue. Pure titanium is the material of choice in craniofacial reconstructive surgery when non-removal of the implant is indicated. As an implant material, pure titanium is preferred because its low density (weight) and elastic modulus (stiffness) are approximately one-half that of stainless steel or cobalt-chromium alloys and the material is corrosion resistant and pliable. Bone plates made from perforated titanium strips and perforated titanium panels can be cut to appropriate configuration and contoured at the time of surgery and, when affixed to bone fragments or bone sections with bone screws, provide solid, stable fixation means during trauma surgery and planned reconstructive surgery.

One preferred form of perforated titanium strips and panels (titanium mesh) includes rows of substantially square perforations which are formed in titanium sheet material by mechanical means (stamping and machining), by electrical arc cutting, and by milling techniques which preserve the stress free condition of the sheet material. The use of titanium mesh with square holes for internal fixation of bone fractures and for reconstructive surgery provides the surgeon with an implantable plate material which can be easily cut to desired contour and shaped or bent to conform to bone fracture and bone reconstruction sites without inducing mechanical stresses into the material because the formability of such mesh is equal along each of the mesh legs which define each of the square holes. Also, as a perforated sheet material the mesh plate structure provides the surgeon with a multiplicity of ready-made holes through which bone screws can be seated and applied to fasten the plate structure to bone fragments and bone sections. Bending of the perforated sheet material does not distort the square holes to the extent that bone screws can not be applied. This is not the case with mesh implant structures wherein the perforations are round holes.

Implantable square-hole titanium mesh structures of the type described above have been fabricated from sheet titanium having a thickness of 1 mm or less. Titanium mesh strips may be obtained with 1 to 4 lines of square perforations in lengths up to 5 inches or more with the perforations arranged uniformly in 30 or more rows. Mesh panels may be obtained with 15 or more lines of square perforations arranged uniformly in 30 more rows. A preferred form of square-hole titanium mesh is that mesh provided with the holes chamfered for receiving the hemispherical underside of low profile bone screws thereby reducing the possibility of screwhead protrusion with respect to the affixation of mesh strips and plates at or near body surfaces.

Another type of implantable perforated titanium strip and panel structure is formed from a thin sheet of titanium as a mesh-like grid of bars or legs forming various geometric open grid shapes. The bars or legs are connected to one-another in land areas or affixation sections of the grid which each include a screw hole through which a bone screw may be applied to affix the grid to bone and/or bone parts. Thus, the grid-type strips and panels may include connected bars or legs which define square, rectangular, triangular, trapezoidal and other plane geometric configurations (or combinations thereof) of open spaces in a single row or multiple rows. The grid bars or legs at each geometric corner of the grid structure (as few as two and as many as six or more legs) are affixed to a land area or affixation section which includes a screw hole. Implantable grid structures of the type described above have been fabricated from titanium sheet material having a thickness of as little as 0.5 mm with the grid legs being as small as 5 mm in length and having a width of 1 mm and the land areas or affixation sections including a screw hole for a screw having a thread diameter of as little as 1 mm. The grid screw holes are chamfered for receiving the hemispherical underside of low profile bone screws. Such grid implant structures are particularly designed to cover with grid structure material per se less than 50% of the bone area to which the structure is applied. In other words, the grid structure is comprised of at least 50% open area.

While the implantable, perforated titanium mesh and grid structures described above are entirely suitable for a multitude of orthognathic and reconstructive surgery procedures and situations, they are not, in and of themselves, always applicable to surgical bone repair and bone regeneration situations wherein it is desirable or necessary to prevent the invasion at the surgical site of body cells which are competitive to or harmful to bone and/or soft tissue repair and regeneration. Further, although such mesh and grid structures are highly desirable in their ability to be bent, contoured and shaped to conform to bone fracture and reconstruction sites, they do not provide means per se to guide tissue regeneration and promote the enlargement of bone tissue.

It is a principal object of the present invention to provide unique perforated metallic implant structures for the internal fixation of bone fractures and for use in orthognathic and reconstructive surgery which have incorporated therewith microporous membrane material which selectively admits biological nutrients to the tissues at the surgical site fixed and protected by the implant structure and which excludes unwanted cells which are harmful and/or competitive to the tissue healing process.

It is a further object of the invention to provide unique mesh- and grid-type composite metallic implant plate structures which are pliable and contourable for use in orthognathic and reconstructive surgery and the correction of cranial defects and which have incorporated therewith a layer of microporous membrane material which selectively prevents the invasion of harmful and/or competitive tissue cells at the surgical site fixed and protected by the implant structure.

It is a still further object of the invention to provide unique biocompatible mesh- and grid-type composite metallic implant plates which are pliable, shapable and contourable, for use in orthognathic and reconstructive surgery, which have incorporated therewith one or more layers of microporous membrane material which selectively admits biological nutrients to tissues at the surgical Site fixed and protected by such plates and which excludes unwanted cells.

It is yet another object of the invention to provide unique biocompatible implant structures, for the surgical internal fixation and protection of bone fractures and for the surgical correction of cranial defects, which are comprised of composites of one or more layers of mesh- or grid-type metallic plates and one or more layers of microporous membrane material which selectively admit desired biological nutrients to the surgical fixation and correction sites and which exclude from such sites unwanted cells which are harmful and/or competitive to the tissue healing process.

It is still another object of the invention to provide unique biocompatible composite implant structures comprised of pliable and contourable mesh- and grid-type perforated metallic plates in sandwich combination with one or more layers of microporous membrane material for use in the guided regeneration and enlargement of bone tissue at surgical sites that have involved orthognathic and reconstructive surgery and the correction of cranial defects.

It is another object of the invention to provide unique biocompatible composite implant structures comprised of pliable and contourable mesh- and grid-type perforated metallic sheet material in sandwich combination with one or more layers of microporous membrane material for tented placement over a bone defect, with attachment thereof to bone about the periphery of the defect, to provide secluded and protected space for the guided regeneration of bone tissue within the defect and for the exclusion of competing cells from the defect area.

Other objects and advantages of the invention will be apparent from the following summary and detailed description of the unique composite implant structures of the invention taken together with the accompanying drawing figures.

SUMMARY OF THE INVENTION

The present invention relates to composite perforated metallic implant structures for use in orthognathic and reconstructive surgery and the correction of cranial defects and for use in the guided regeneration and enlargement of bone tissue. The composite implant structures of the invention are basically comprised of one or more pliable and contourable mesh- and grid-type perforated, biocompatible metallic plates in combination with one or more layers of microporous membrane material. The mesh- and grid-type metallic components of the composite structures may be fabricated from sheets of stainless steel, cobalt-chromium alloys and pure titanium and may take the form of strips and panels for internal bone and bone part fixation, mandibular bone reconstruction trays and cages, contoured skull cap covers, and numerous other implant forms, The preferred metal for such implant structures is titanium, as hereinbefore indicated.

The microporous membrane components of the implantable composite structures of the invention are preferably layers of biologically and chemically inert ultrafiltration material in sheet form comprised of randomly arranged polytetrafluoroethylene (PTFE) fibers with or without high-density polyethylene backing. Such material is available as "Fluoropore" membrane filter material from the Millipore Corporation in pore size ranges from 0.2 to 3.0 microns (a most preferred pore size for the membrane component of the present composite implant structures being 0.5 microns). An alternative microporous membrane material, for utilization in the composite structures of the invention, is available as "Gore-Tex" expanded PTFE barrier material designed to be cell occlusive even to bacteria. This form of PTFE microporous filter material is available from W. L. Gore & Associates, Inc. and has a like pore size range. PTFE and expanded PTFE microporous membrane materials as biomaterials have a long and well-documented medical history.

The composite implant structures of the invention may include sandwich type structures having outer layer components of mesh- or grid-type perforated metallic sheet material and an inner layer of the microporous membrane material or having outer layer components of microporous membrane material and an inner layer of mesh- or grid-type perforated metallic sheet material. Alternatively, the composite implant structures may include a single layer of mesh- or grid-type perforated metallic sheet material and a layer of the microporous membrane material. It is also within the scope of the present invention that the layer or layers of perforated metallic sheet material of the composite implant structure may be comprised of metallic sheet material having round hole mesh-type perforations arranged in uniform rows and lines, or rectangular mesh-type perforations that are off-set with respect to each other in adjacent rows, or even perforations that are isosceles in shape and arranged in rows of alternating triangular orientation. Also, woven wire mesh material, particularly woven titanium wire material having from about 8 to about 18 openings per linear inch in both directions, may comprise the perforated sheet material.

The composite layered structures of the invention may be given unitary structural integrity by heat fusion bonding of the layer or layers of membrane material to the layer or layers of perforated metallic sheet material or by bonding the membrane and metallic layers together via a biocompatible adhesive material such as iso-butyl-2-cyano-acrylate. In either type of bonding of membrane material to perforated metallic sheet material care must be taken to assure that the fibers and pores of the membrane material, interfacing the areas of the perforation openings of the metallic sheet material, are not adversely affected. Thus, fibers in such interfacing areas must not be heat bonded together with the result that the pore size and number of pores is restricted, and the fibers must not be bonded together by adhesive material or the pores filled with adhesive, thereby changing the filtration and cell barrier capabilities and characteristics of the membrane material.

In accordance with the present invention the composite nature of the implantable structures comprised of one or more layers of perforated metallic sheet material (mesh- and grid-types) and one or more layers of microporous membrane material may be maintained merely by the mechanical fastening means used to place and secure such structures to bone and bone parts and over bone defects.

It is to be understood that the composite perforated implant structures of the present invention are particularly applicable to orthognathic and reconstructive surgical situations and to cranial defect problems where guided regeneration and enlargement of bone tissue is an important objective with the eventual removal of the implant structure and its microporous membrane material. The composite nature of the implant structure provides the shapability afforded by pliable perforated metallic plates and thereby the desired support for the membrane material to provide appropriate space or tenting for bone regeneration and to prevent membrane collapse or movement which may obstruct osteogenesis.

BRIEF DESCRIPTION OF THE DRAWING FIGURES

FIG. 6 is a top plan view of a fourth alternative form of composite perforated implant structure in accordance with the invention comprised of a single layer of biocompatible woven wire cloth mesh material in combination with a single layer of microporous membrane material;

FIG. 7 is a cross-sectional view of the composite layers of woven metallic wire cloth mesh material and microporous membrane material of FIG. 6 taken on line 7—7 of FIG. 6;

FIG. 8 is a perspective view of another form of composite perforated implant structure of the invention comprised of an outer tube of metallic mesh-type sheet material within which is positioned a layer of microporous membrane material; and FIG. 9 is a perspective view of a mandibular reconstruction tray implant of composite structure in accordance with the invention, as applied to a sectioned mandible, the tray being comprised of a mandibular shaped biocompatible metallic mesh-type plate within which is affixed and supported a layer of microporous membrane material.

DETAILED DESCRIPTION OF THE INVENTION

Figure 1:
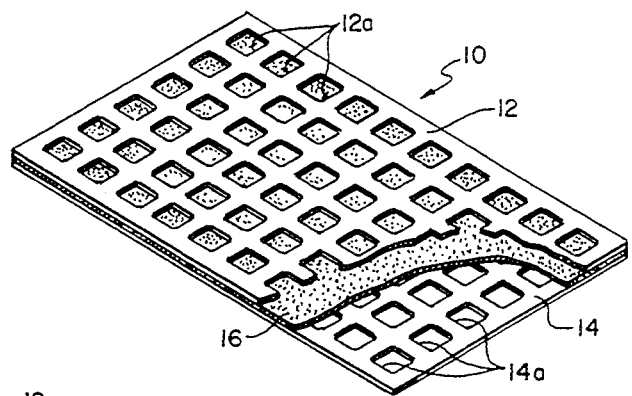
FIG. 1 is a top perspective view, partially cut away, of a composite perforated implant plate structure in accordance with the present invention and comprised of outer layers square hole mesh-type biocompatible metallic sheet material in sandwiching combination with an intermediate layer of microporous membrane material.
Figure 2:
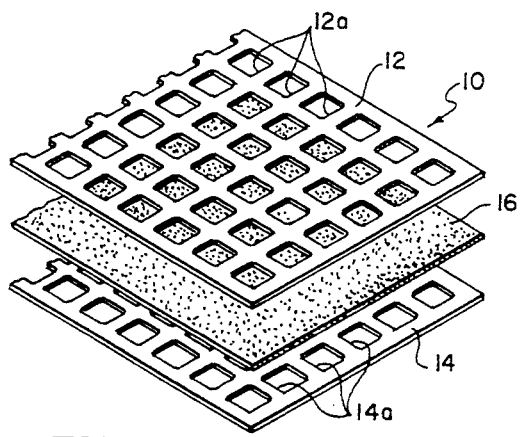
FIG. 2 is a partial exploded top perspective view of the implant plate structure of FIG. 1.

Referring to FIGS. 1 and 2 of the drawings, there is illustrated a composite perforated metallic implant plate structure 10 in accordance with the invention. The implant plate structure 10 basically comprises a sandwich-type composite arrangement of outer layers 12 and 14 of perforated biocompatible metallic mesh-type sheet material and an intermediate layer 16 of non-resorbable microporous membrane material. In FIG. 1 the implant structure 10 is presented in a top perspective view as a unitary composite plate structure with portions of the upper metallic mesh-type layer 12 and intermediate microporous membrane layer 16 cut away. FIG. 2 presents the same implant structure 10 in an exploded partial top perspective view. The upper and lower metallic mesh-type sheet material layers 12 and 14 are preferably fabricated from pure titanium sheet material and include uniformly sized and spaced rows and lines of square perforations 12a and 14a, respectively.

The metallic layers 12 and 14 of the composite implant structure range in thickness from about 0.05 mm to about 2.0 mm and are pliable so that the composite implant plate structure 10 may be readily shaped and contoured to fit bone and bone defect areas. The plate structure may also be cut down to appropriate size and trimmed in its peripheral areas to a desired margin shape. The Intermediate non-resorbable microporous membrane layer 16 of the implant structure 10 is preferably comprised of random fiber matted forms of "Teflon" material, i.e., polytetrafluoroethylene (PTFE), or an expanded form thereof termed e-PTFE. Such materials are biologically and chemically inert and are known for their excellent ultrafiltration properties. As previously described, the layer of microporous membrane material of the implant structure of the invention acts as a harrier and protector of the bony defect at the surgical site over which the structure is placed and selectively admits biological nutrients to tissues at the surgical site and excludes unwanted cells. So that the composite implant structure 10 may be readily affixed to bone and bone parts proximate the bony defect it is to protect, upper and lower metallic layers 12 and 14 of the structure must be aligned, with their respective mesh openings matched up, that bone affixation screws may be applied through structure. As earlier indicated, the layered implant structure may be maintained as a composite unit by adhering the layer of membrane material to the metallic layers by heat fusion of the membrane fibers to the metallic sheet material or adhesion of the layers to one-another by an appropriated adhesive material. Alternatively, the intermediate membrane layer may be held in composite arrangement with the outer metallic layers by the bone screws used to affix the implant structure to surrounding bone at the surgical site.

Figure 3:
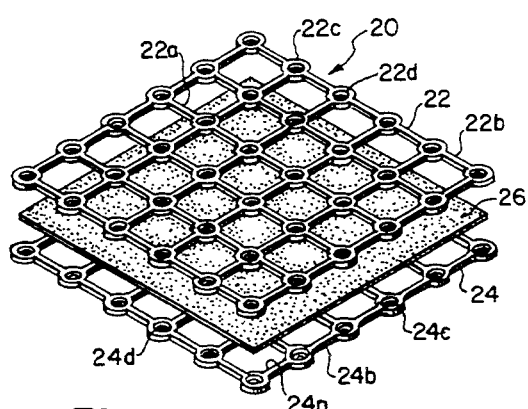
FIG. 3 is an exploded top perspective view of an alternative form of composite perforated implant plate structure in accordance with the invention comprised of outer layers of grid-type biocompatible metallic sheet material in sandwiching combination with an intermediate layer of microporous membrane material.

FIG. 3 presents, in an exploded top perspective view, an alternative form of a composite perforated implant plate structure 20 of the invention wherein the intermediate layer 26 of microporous membrane material is sandwiched be outer layers 22 and 24 of grid-type biocompatible metallic sheet material. The upper grid-type member 22 of the composite structure 20 includes grid legs 22a and 22b which form square grid perforations with the corners of each square opening of the grid including land areas or affixation sections 22c which each include a screw hole 22d through which a bone screw may applied to affix the stricture to bone and/or bone parts. The lower grid-type member 24 includes like grid legs 24a and 24b defining square openings and corner land areas or affixation sections 24c including screw holes 22d. So that the composite structure 20 may be affixed to the bone and bone parts proximate the are defect area it is to protect, the upper and lower grid-type layers 22 and 24 must be aligned with their respective grid openings matched up so that bone affixation screws may be applied through the structure. As in the case of the implant structure shown in FIGS. 1 and 2, the layers of the FIG. 3 composite implant structure may be maintained in their composite layered orientation by adhesive or heat fusion bonding or by the screw fasteners applied through the structure to the supportive bone at the surgical site.

Figure 4:
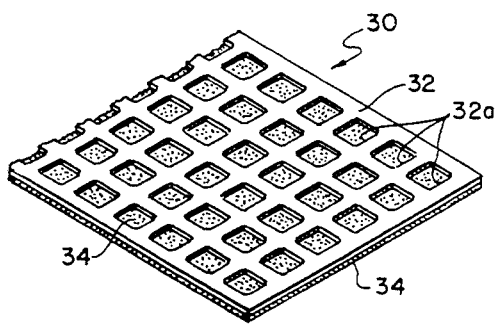
FIG. 4 is a top perspective view of a further alternative form of composite perforated implant plate structure of the invention comprised of a single layer of mesh-type biocompatible metallic sheet material in combination with a single layer of microporous membrane material.
Figure 5:
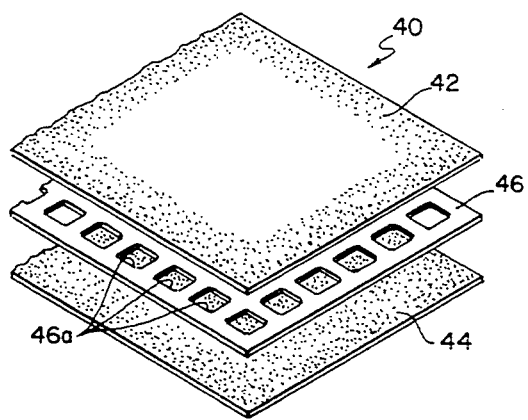
FIG. 5 is an exploded top perspective view of a third alternative form of composite perforated implant plate structure of the invention comprised of outer layers of microporous membrane material in sandwiching combination with an intermediate layer of mesh-type biocompatible metallic sheet material.

The composite implant plate structure 30 illustrated in FIG. 4 is comprised of a single layer 32 of mesh-type biocompatible metallic sheet material (with square mesh openings 32a) bonded to, or mechanically held to, a single layer 34 of microporous membrane material. The composite implant structure 40 illustrated in FIG. 5 is comprised of outer layers 42 and 44 of microporous membrane material bonded to, or mechanically held to, a single intermediate layer 46 of mesh-type biocompatible metallic sheet material.

In FIG. 6 and 7 there is illustrated a further form of composite perforated implant structure 50 in accordance with the present invention. As shown in the top plan view of FIG. 6, the composite implant structure is comprised of a single layer 52 of woven cloth mesh material having open weave openings 52a defined by the interwoven biocompatible metallic wires 52b and 52c with such woven mesh layer bonded to, or mechanically held to, a single layer 54 of microporous membrane material. The composite implant structure 50 of FIG. 6 is further illustrated in the cross-sectional view of the structure presented in FIG. 7.

An alternative form of composite perforated implant structure, in accordance with the present invention, is illustrated in FIG. 8 and consists of a prosthetic implant structure 60, shown in perspective, which may be used to replace tubular body parts, i.e., arteries, esophagus, etc. The composite tubular implant structure 60 is comprised of an outer cylindrical layer 62 of mesh-type biocompatible metallic sheet material (including square perforations 62a) and an inner tubular layer 64 of microporous membrane material of the type hereinbefore described. The non-resorbable microporous membrane material of the composite structure may be held in its tubular configuration merely by the surrounding tubular configuration of the metallic mesh-type sheet material.

Another form of composite perforated implant structure in accordance with the invention is shown in the perspective view of FIG. 9 in association with a section mandible "m." The implant structure consists of a mandibular reconstruction tray or crib 70 formed from mesh-type biocompatible metallic sheet material 72 (including square hole perforations 72a) within which is positioned a layer 74 of microporous membrane material of the type previously described. The tray or crib 70 is affixed to right and left mandible stubs or stumps via appropriate bone screws (not shown). The membrane material 74 is maintained within the tray by heat fusion or adhesive bonding to the perforated metallic sheet material 72 or merely by the bone screws which fasten the tray to the mandible stubs or stumps. The tray structure 70, placed under reconstructive surgery practice, will normally be packed with bone marrow, covered by an enclosing portion of the membrane material (not shown), and covered with soft tissue.

It should be understood that, although not specifically illustrated, the composite implant structures of the present invention are particularly applicable to solving known surgical reconstruction problems regarding guided tissue regeneration in anticipation of, or during, the placement of endosseous dental implants where ridge maintenance, regeneration and/or augmentation is critical to the success of such implants. Thus, pliable, biocompatible composite metallic implant structures of the invention can be utilized as barriers to unwanted cells and at the same time can provide tenting means to maintain edentulous spaces within which regenerated bone tissue growth is desired for eventual placement of dental tooth root implants.

It should also be understood that the microporous membrane material comprising one or more layers of the composite implant structure of the invention, in addition to being constituted of polytetrafluoroethylene fibers, may be constituted of biologically and chemically inert microporous membrane material including mixtures of cellulose acetate and cellulose nitrate fibers and polyvinylidine difluoride fibers.

While the invention has been described in connection with a variety of disclosed composite implant structures utilizing combinations of one or more layers of perforated biocompatible metallic sheet material and one or more layers of microporous membrane material, for internal fixation of bone fractures, reconstructive surgery, correction of cranial defects, and the guided regeneration and enlargement of bone tissue, many modifications of the invention will be apparent to those skilled in the art. Accordingly, such modifications are to be included within the spirit and scope of the invention as defined by the following claims.

What I claim is:

1. A composite surgical implant structure for use in orthognathic and reconstructive surgery and for the correction of cranial defects of human patients comprising:

a) at least one layer of perforated and pliable, biocompatible metallic sheet material wherein the perforations are of a size such that bone screws may be inserted therethrough and into hard and soft tissues of a human patient; and b) at least one layer of biologically and chemically inert microporous membrane sheet material of like size and configuration in intimate contact with, supported by, and covering said at least one layer of perforated metallic sheet material, said at least one layer of microporous membrane material being comprised of randomly dispersed polytetrafluoroethylene fibers having a pore size in the range of from about 0.2 to about 3.0 microns whereby desired biological nutrients are permitted passage through the pores of said membrane material and the perforations of said metallic sheet material of said implant structure to underlying hard and soft tissues of said human patient and unwanted biological cells and bacteria are precluded from passage through said implant structure to said tissues.

2. The composite surgical implant structure as claimed in claim 2 wherein said membrane material has a pore size in the range of from about 0.4 to about 0.6 microns.

3. The composite surgical implant structure as claimed in claim 1 wherein said at least one layer of perforated and pliable, biocompatible metallic sheet material is comprised of a mesh-type metallic plate including a multiplicity of square perforations arranged uniformly in lines and rows.

4. The composite surgical implant structure as claimed in claim 1 wherein said at least one layer of perforated and pliable, biocompatible metallic sheet material is comprised of a metallic plate having a grid of legs forming a multiplicity of open geometric spaces with said legs connected to one-another in affixation sections which each include a screw hole for accepting a bone screw as may be inserted therethrough, said open spaces comprising at least 50% of the surface area of said metallic plate.

5. The composite surgical implant structure as claimed in claim 1 wherein said perforated, biocompatible metallic sheet material is comprised of a pliable perforated metal plate off pure titanium having a thickness range of from about 0.05 to about 2.0 mm.

6. The composite surgical implant structure as claimed in claim 1 wherein said implant structure is comprised of a single layer of said perforated and pliable metallic sheet material and a single layer of said microporous membrane sheet material, said layers being affixed to one another by means selected from the group consisting of: biocompatible adhesives having an adhesive affinity for said perforated metallic sheet material and said membrane material and applied only the interfacing surface areas of said metallic shear material leaving the pores of said membrane material proximate the perforations of said metallic sheet material open, heat fusion of the fibers of said membrane material to the interfacing surface areas of said metallic sheet material, and bone screws interacting between said layers.

7. The composite surgical implant structure as claimed in claim 1 wherein said implant structure is comprised of a sandwich-type arrangement of layers including outer layers of said perforated metallic sheet material and an intermediate layer of said microporous membrane sheet material.

8. The composite surgical implant structure as claimed in claim 1 wherein said implant structure is comprised of a sandwich-type arrangement of layers including outer layers of said microporous membrane sheet material and an intermediate layer of said perforated metallic sheet material.

9. The composite surgical implant structure as claimed in claim 1 wherein said perforated, biocompatible metallic sheet material is selected from the group consisting of titanium, titanium alloys, cobalt-chrome alloys and stainless steel.

10. The composite surgical implant structure as claimed in claim 1 wherein said perforated and pliable, biocompatible metallic sheet material is comprised of pliable woven titanium wire mesh material having from about 8 to about 16 openings per linear inch in both directions.

11. A composite surgical implant structure for use in orthognathic and reconstructive surgery, for the correction of cranial defects, and for the guided regeneration and enlargement of bone tissue of human patients, said implant structure comprising:

a) at least one layer of biocompatible and pliable metallic sheet material selected from the group consisting titanium, titanium alloys, cobalt-chrome alloys and stainless steel, said metallic sheet material including a multiplicity uniformly arranged mesh-type perforations of a size such that mechanical fasteners may be inserted therethrough and into bone tissue of a human patient; and b) at least one layer of biologically and chemically inert microporous membrane sheet material of like size configuration comprised of randomly dispersed polytetrafluoroethylene fibers, said at least one layer of said microporous membrane sheet material being in intimate contact with, supported by, and covering said at least one layer of metallic sheet material, and said at least one layer of membrane sheet material having a pore size in the range of about 0.2 to about 3.0 microns whereby desired biological nutrients for bone regeneration are permitted passage through the pores of said membrane material and the perforations of said metallic sheet material of said implant structure underlying bone and unwanted biological cells and bacteria are precluded from passage through said implant structure to underlying bone.

12. The composite surgical implant structure as claimed in claim 11 wherein said microporous membrane material has pore size in the range of from about 0.4 to about 0.6 microns.

13. The composite surgical implant structure as claimed in claim 11 wherein said layer of metallic sheet material is comprised of a plate of pure titanium having a thickness range of from about 0.05 to about 2.0 mm and said layer of microporous membrane material has a thickness range of from about 0.1 to about 1.0 min.

14. The composite surgical implant structure as claimed in claim 11 wherein said implant structure is comprised of a sandwich-type arrangement of three layers including outer layers of said metallic sheet material and an intermediate layer of said microporous membrane material.

15. The composite surgical implant structure as claimed in claim 11 wherein said implant structure is comprised of a sandwich-type arrangement of three layers including outer layers of said microporous membrane material and an intermediate layer of said metallic sheet material.

16. A composite surgical implant structure for use in orthognathic and reconstructive surgery, for the correction of cranial defects, and for reconstructive preprosthetic oral and maxillofacial surgery of bone tissue of human patients comprising:

a) at least one layer of perforated and pliable, biocompatible metallic sheet material wherein the perforations in said sheet material are of a size such that mechanical fasteners may be inserted therethrough and into bone tissue of a human patient; and b) at least one layer of microporous membrane sheet material of like size and configuration in intimate contact with, supported by, and covering said at least one layer of said perforated metallic sheet material, said microporous membrane sheet material being selected from the group of biologically and chemically inert sheet materials consisting of polytetrafluoroethylene fibers, mixtures of cellulose acetate and cellulose nitrate fibers and polyvinylidine difluoride fibers, and said at least one layer of microporous membrane sheet material having a pore size in the range of from about 0.2 to about 3.0 microns whereby desired biological nutrients are permitted passage through the pores of said membrane material and the perforations of said metallic sheet material of said implant structure to underlying bone tissues of said patient and unwanted biological cells and bacteria are precluded from passage through said implant structure to said tissues.

* * * * *